United States Patent
Horii

(10) Patent No.: US 10,376,944 B2
(45) Date of Patent: Aug. 13, 2019

(54) PIPE JOINING BODY, TREATMENT TOOL, AND JOINING METHOD

(71) Applicant: OLYMPUS CORPORATION, Hachioji-shi, Tokyo (JP)

(72) Inventor: Shingo Horii, Sagamihara (JP)

(73) Assignee: OLYMPUS CORPORATION, Tokyo (JP)

(*) Notice: Subject to any disclaimer, the term of this patent is extended or adjusted under 35 U.S.C. 154(b) by 320 days.

(21) Appl. No.: 15/236,589

(22) Filed: Aug. 15, 2016

(65) Prior Publication Data
US 2016/0346826 A1    Dec. 1, 2016

Related U.S. Application Data

(63) Continuation of application No. PCT/JP2014/081685, filed on Dec. 1, 2014.

(30) Foreign Application Priority Data

Feb. 20, 2014 (JP) ................. 2014-030533

(51) Int. Cl.
*A61B 17/08* (2006.01)
*A61B 17/12* (2006.01)
(Continued)

(52) U.S. Cl.
CPC ............ *B21D 39/04* (2013.01); *A61B 1/0011* (2013.01); *A61B 17/08* (2013.01); *A61B 17/083* (2013.01);
(Continued)

(58) Field of Classification Search
CPC ..... B21D 39/04; A61B 1/0011; A61B 17/083; A61B 17/08; A61B 17/1285; A61B 1/018;
(Continued)

(56) References Cited

U.S. PATENT DOCUMENTS

| 1,693,839 A | 12/1928 | Faudi |
| 4,396,213 A | 8/1983 | Hawkins |

(Continued)

FOREIGN PATENT DOCUMENTS

| CN | 102448378 A | 5/2012 |
| DE | 3223004 C2 | 11/1992 |

(Continued)

OTHER PUBLICATIONS

JP H0399731 EPO English Machine Translation; Yokoo et al.; Method for Calking and Joining Shaft and Thin Wall Tube; Sep. 21, 2018; pp. 1-3.*

(Continued)

*Primary Examiner* — Bayan Salone
(74) *Attorney, Agent, or Firm* — Holtz, Holtz & Volek PC

(57) ABSTRACT

Provided is a pipe joining body in which a wire rod and a tubular member are joined. The wire rod includes a concave portion formed by plastically deforming a part of an outer periphery of the wire rod. The tubular member includes a deformed portion that is formed so as to enter the concave portion by inserting the wire rod into the tubular member and by pressing a portion of the tubular member covering the concave portion toward the concave portion to plastically deform the portion. A maximum displacement amount of the tubular member when the deformed portion is formed is not larger than a maximum displacement amount of the wire rod by the plastic deformation when the concave portion is formed. The concave portion is formed by bringing a mold having a convex surface into contact with the part of the outer periphery of the wire rod to press.

9 Claims, 12 Drawing Sheets

(51) Int. Cl.
*A61B 1/00* (2006.01)
*F16L 13/14* (2006.01)
*B21D 39/04* (2006.01)
*A61B 17/128* (2006.01)
*A61B 1/018* (2006.01)
*A61B 17/00* (2006.01)
*A61B 17/064* (2006.01)

(52) U.S. Cl.
CPC .......... *A61B 17/1285* (2013.01); *F16L 13/14* (2013.01); *F16L 13/141* (2013.01); *A61B 1/018* (2013.01); *A61B 2017/00477* (2013.01); *A61B 2017/00526* (2013.01); *A61B 2017/00867* (2013.01); *A61B 2017/0649* (2013.01)

(58) Field of Classification Search
CPC .. A61B 2017/0649; A61B 2017/00477; A61B 2017/00526; A61B 2017/00867; Y10T 29/49931; Y10T 29/49936
USPC ......... 29/517, 596; 123/197.1, 197.3, 197.4; 606/1, 53, 76
See application file for complete search history.

(56) References Cited

U.S. PATENT DOCUMENTS

| | | | |
|---|---|---|---|
| 4,572,022 | A | 2/1986 | Mettler |
| 6,474,701 | B1 | 11/2002 | Bowles et al. |
| 8,858,576 | B2 | 10/2014 | Takahashi et al. |
| 2010/0010520 | A1 | 1/2010 | Takahashi et al. |
| 2012/0029278 | A1* | 2/2012 | Sato ................. A61B 17/00234 600/104 |
| 2014/0058419 | A1 | 2/2014 | Takahashi et al. |
| 2016/0089711 | A1* | 3/2016 | Kawahara ............ B21D 39/048 29/517 |

FOREIGN PATENT DOCUMENTS

| | | | | |
|---|---|---|---|---|
| EP | 2998632 | A1 * | 3/2016 | .......... B21D 39/048 |
| JP | 03099731 | A * | 4/1991 | |
| JP | 03099731 | A | 4/1991 | |
| JP | 08156747 | A * | 6/1996 | ............ B60S 1/0413 |
| JP | 08156747 | A | 6/1996 | |
| JP | 2000355207 | A | 12/2000 | |
| JP | 2009066408 | A | 4/2009 | |
| JP | 2010017542 | A | 1/2010 | |
| WO | 9741377 | A1 | 11/1997 | |
| WO | 2014184832 | A1 | 11/2014 | |

OTHER PUBLICATIONS

JP H08156747 EPO English Machine Translation; Abe; Pipe Fastening Method; Sep. 21, 2018; pp. 1-4.*
Chinese Office Action (and English translation thereof) dated Nov. 15, 2017, issued in counterpart Chinese Application No. 201480075820. 5.
International Search Report (ISR) and Written Opinion dated Mar. 3, 2015 issued in International Application No. PCT/JP2014/ 081685.
Chinese Office Action (and English translation thereof) dated Mar. 29, 2017, issued in counterpart Chinese Application No. CN 201480075820.5.
German Office Action dated Sep. 21, 2018 (and English translation thereof) issued in counterpart German Application No. 112014006389. 4.

* cited by examiner

PIPE JOINING BODY, TREATMENT TOOL, AND JOINING METHOD

CROSS REFERENCES TO RELATED APPLICATIONS

This application is a continuation of PCT international application Ser. No. PCT/JP2014/081685, filed on Dec. 1, 2014 which designates the United States, incorporated herein by reference, and which claims the benefit of priority from Japanese Patent Application No. 2014-030533, filed on Feb. 20, 2014, incorporated herein by reference.

BACKGROUND

1. Technical Field

The disclosure relates to a pipe joining body in which a wire rod and a pipe are joined, a treatment tool having the pipe joining body, and a joining method.

2. Related Art

Swaging processing to insert a wire rod into a pipe and swage the pipe and the wire rod from an outer periphery of the pipe is conventionally known as technology of swaging metallic wire rod and pipe. However, in the conventional swaging processing, a biting amount of a pipe member into the wire rod is small, so that there is a case in which sufficient joining force cannot be obtained.

In order to address such a situation, the joining force between a pipe attaching portion and the pipe is improved easily by swaging the pipe by using a mold having four teeth so as to closely adhere to locking grooves formed in advance on the pipe attaching portion in JP 08-156747 A.

SUMMARY

In some embodiments, provided is a pipe joining body in which a wire rod and a tubular member are joined. The wire rod includes at least one concave portion formed by plastically deforming a part of an outer periphery of the wire rod. The tubular member includes at least one deformed portion that is formed so as to enter the at least one concave portion by inserting the wire rod into the tubular member and by pressing a portion of the tubular member covering the at least one concave portion from an outer periphery of the tubular member toward the at least one concave portion to plastically deform the portion. A maximum displacement amount of the tubular member when the deformed portion is formed is not larger than a maximum displacement amount of the wire rod by the plastic deformation when the concave portion is formed. The at least one concave portion is formed by bringing a transfer mold having a convex transfer surface into contact with the part of the outer periphery of the wire rod to press. The at least one deformed portion is formed by bringing a transfer mold having a transfer surface of a same shape as that used for the wire rod, into contact with the outer periphery of the tubular member to press.

In some embodiments, provided is a treatment tool for an endoscope that is configured to be inserted into a living body when in use. The treatment tool includes the pipe joining body.

In some embodiments, provided is a pipe joining body in which a wire rod and a tubular member are joined. The wire rod includes at least one concave portion formed by plastically deforming a part of an outer periphery of the wire rod. The tubular member includes at least one deformed portion that is formed so as to enter the at least one concave portion by inserting the wire rod into the tubular member and by pressing a portion of the tubular member covering the at least one concave portion from an outer periphery of the tubular member toward the at least one concave portion to plastically deform the portion. A maximum displacement amount of the tubular member when the deformed portion is formed is not larger than a maximum displacement amount of the wire rod by the plastic deformation when the concave portion is formed. Hardness of the tubular member is lower than hardness of the wire rod.

In some embodiments, provided is a treatment tool for an endoscope that is configured to be inserted into a living body when in use. The treatment tool includes the pipe joining body.

In some embodiments, provided is a method of joining a wire rod to a tubular member. The method includes: forming at least one concave portion by plastically deforming a part of an outer periphery of the wire rod; and forming at least one deformed portion so as to enter the at least one concave portion by inserting the wire rod into the tubular member and by pressing a portion of the tubular member covering the at least one concave portion from an outer periphery of the tubular member toward the at least one concave portion to plastically deform the portion. A maximum displacement amount of the tubular member in forming the deformed portion is not larger than a maximum displacement amount of the wire rod in forming the concave portion. The forming of the concave portion includes forming the at least one concave portion by bringing a transfer mold having a convex transfer surface into contact with the part of the outer periphery of the wire rod to press. The forming of the deformed portion includes forming the at least one deformed portion by bringing a transfer mold having a transfer surface of a same shape as that used for the wire rod, into contact with the outer periphery of the tubular member to press.

In some embodiments, provided is a method of joining a wire rod to a tubular member. The method includes: forming at least one concave portion by plastically deforming a part of an outer periphery of the wire rod; and forming at least one deformed portion so as to enter the at least one concave portion by inserting the wire rod into the tubular member and by pressing a portion of the tubular member covering the at least one concave portion from an outer periphery of the tubular member toward the at least one concave portion to plastically deform the portion. A maximum displacement amount of the tubular member in forming the deformed portion is not larger than a maximum displacement amount of the wire rod in forming the concave portion. Hardness of the tubular member is lower than hardness of the wire rod.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, embodiments of a pipe joining body, a treatment tool, and a joining method according to the present invention will be described in detail with reference to the drawings. The present invention is not limited by the embodiments. The same reference signs are used to designate the same elements throughout the drawings. The drawings are schematic, so that it is noted that dimensional relationship between the elements and a ratio of the elements might be different from actual ones. The dimensional relationship and the ratio might be different among the drawings.

First Embodiment

Figure 1A:
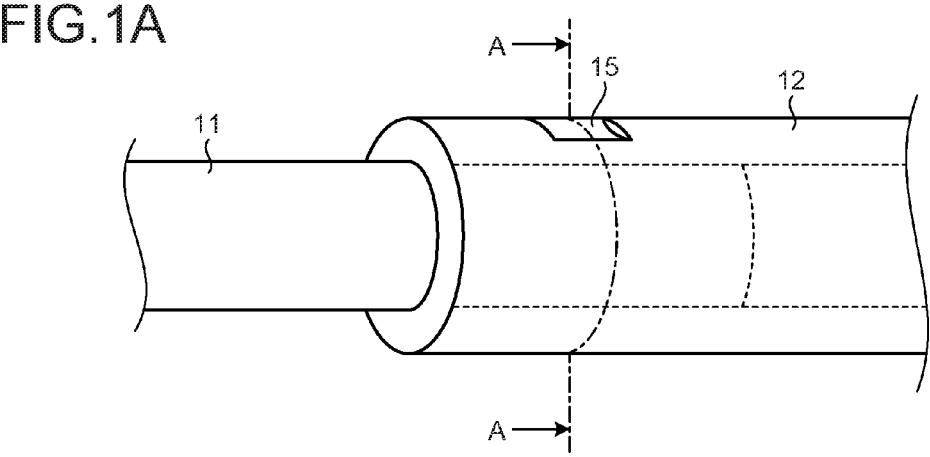
FIGS. 1A and 1B are schematic views illustrating a structure of a pipe joining body according to a first embodiment of the present invention.
Figure 1B:
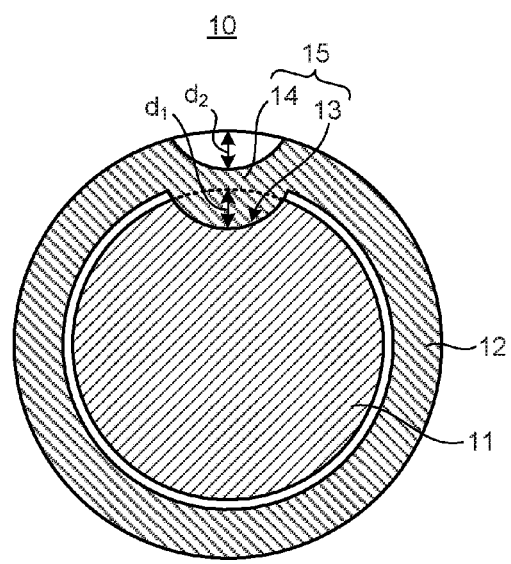

FIGS. 1A and 1B are schematic views illustrating a structure of a pipe joining body according to a first embodiment of the present invention. FIG. 1A is a perspective, external view of the pipe joining body and FIG. 1B is a cross-sectional view taken along A-A in FIG. 1A.

As illustrated in FIGS. 1A and 1B, a pipe joining body 10 according to the first embodiment is provided with a wire rod 11 and a tubular member 12 formed of metal or alloy. A concave portion 13 formed by plastic deformation of the wire rod 11 is provided on a part of an outer periphery of the wire rod 11. A deformed portion 14 formed such that the tubular member 12 is plastically deformed to enter the concave portion 13 is provided on a part of an outer periphery of the tubular member 12. The concave portion 13 and the deformed portion 14 constitute a joining portion 15 which joins the wire rod 11 to the tubular member 12.

The deformed portion 14 may fit in the concave portion 13 without clearance as illustrated in FIG. 1B or may be slightly separated from the concave portion 13. In this manner, by allowing the deformed portion 14 to fit or loosely fit in the concave portion 13, the wire rod 11 and the tubular member 12 are joined to each other. Although the joining portion 15 formed of the concave portion 13 and the deformed portion 14 is provided at one location in the first embodiment, the number of the joining portions 15 is not especially limited.

A diameter of the wire rod 11 is not especially limited; the first embodiment is applicable to the wire rod having a fine diameter of one millimeter or smaller to the wire rod having a diameter of several centimeters or larger. An outer diameter and an inner diameter of the tubular member 12 are not especially limited as long as the member has the inner diameter into which the wire rod 11 is insertable and a thickness sufficient for forming the deformed portion 14 by the plastic deformation. Although there is a slight clearance between the outer periphery of the wire rod 11 and an inner periphery of the tubular member 12 in FIG. 1B, it is also possible to determine the diameter of the wire rod 11 and the inner diameter of the tubular member 12 such that the members are fit together without clearance. In contrast, the clearance between the outer periphery of the wire rod 11 and the inner periphery of the tubular member 12 may be made larger than that in FIG. 1B as long as the deformed portion 14 is not dropped out from the concave portion 13.

Shapes of the concave portion 13 and the deformed portion 14 are determined according to a shape of a mold attached to a swaging processing machine to be described later. In the first embodiment, the concave portion 13 has a substantially rectangular shape when the wire rod 11 before the joining is viewed from a side surface and has a substantially arc-liked shape in cross section orthogonal to a longitudinal direction of the wire rod 11. Similar to the concave portion 13, the deformed portion 14 also has a substantially rectangular shape when the tubular member 12 is viewed from a side surface and has a substantially arc-like shape in cross section orthogonal to a longitudinal direction of the tubular member 12.

A maximum displacement amount $d_2$ of the tubular member 12 by the plastic deformation when the deformed portion 14 is formed is as large as or smaller than a maximum displacement amount $d_1$ of the wire rod 11 by the plastic deformation when the concave portion 13 is formed. According to this, the thickness in the deformed portion 14 of the tubular member 12 may be kept to the same thickness as that in other portions, thereby inhibiting partial deterioration in strength. In the first embodiment, $d_1=d_2$ is satisfied and the deformed portion 14 is plastically deformed such that the deformed portion 14 conforms to the concave portion 13 without clearance.

Materials of the wire rod 11 and the tubular member 12 are not especially limited as long as they are plastically-deformable metal or alloy. The wire rod 11 and the tubular member 12 may be formed of the same type of metal or alloy or of a combination of different types of metal or alloy.

As an example of the combination of the materials, for example, a material of the tubular member 12 with hardness lower than that of the wire rod 11 may be combined with the wire rod 11, for example. Specifically, there is a combination of the wire rod 11 of stainless steel (SUS) and the tubular member 12 of same SUS with hardness decreased by annealing. Alternatively, there also is the combination of the wire rod 11 of titanium alloy such as Ti-6Al-4V and the tubular member 12 of same titanium alloy with hardness decreased by annealing.

When different types of metal or alloy are used for the wire rod 11 and the tubular member 12, an SUS material including high-tensile steel such as stainless steel for spring, precipitation-hardening stainless steel, and high-carbon stainless steel, titanium alloy, tungsten, molybdenum, cobalt alloy and the like serve as the material of the wire rod 11. In contrast, a material with hardness lower than that of the wire rod 11 such as an SUS material with hardness decreased by annealing, titanium alloy with hardness decreased by annealing, gold alloy, silver alloy, and platinum is preferably used for the tubular member 12.

Figure 2:
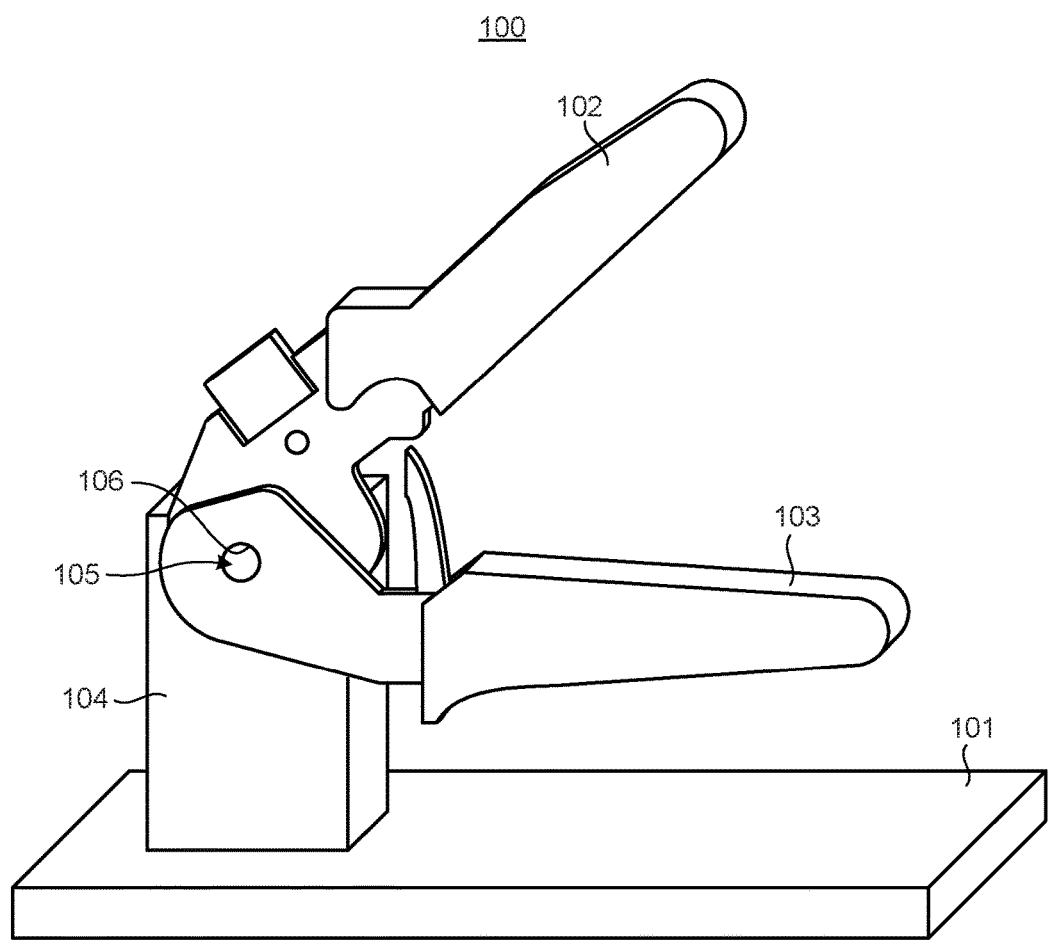
FIG. 2 is a schematic diagram illustrating an example of a swaging processing machine used in a joining method according to the first embodiment of the present invention.
Figure 3:
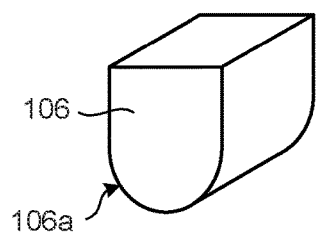
FIG. 3 is a schematic diagram illustrating an example of a mold used in the joining method according to the first embodiment of the present invention.

Next, a joining method according to the first embodiment of the present invention will be described. FIG. 2 is a schematic diagram illustrating an example of the swaging processing machine used in the joining method according to the first embodiment. FIG. 3 is a schematic diagram illustrating an example of the mold used in the joining method.

A swaging processing machine 100 illustrated in FIG. 2 is provided with a seat 101, a supporting section 104 which supports pressing sections 102 and 103 to fix on the seat 101, a processing section 105 into which the wire rod 11 and the tubular member 12 as a workpiece are inserted, and a mold 106 attached to the processing section 105. The swaging processing machine 100 may plastically deform a workpiece by pressing the workpiece inserted into the processing section 105 with the mold 106 through operation of the pressing sections 102 and 103.

As illustrated in FIG. 3, the mold 106 is a columnar transfer mold including a transfer surface 106a having an arc-like curved shape on an end abutting on the workpiece as viewed from a side surface in a transverse direction. By bringing the transfer surface 106a into contact with the wire rod 11 and the tubular member 12 and pressing the same, it is possible to partially plastically deform the outer periphery to form the concave portion 13 and the deformed portion 14.

Figure 4A:
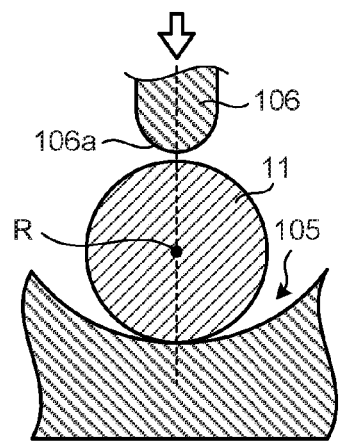
FIGS. 4A to 4D are schematic diagrams for illustrating the joining method according to the first embodiment of the present invention.
Figure 4B:
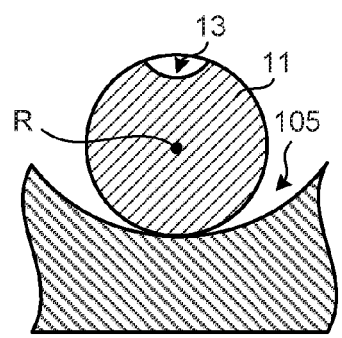

FIGS. 4A to 4D are schematic diagrams for illustrating the joining method according to the first embodiment. First, the mold 106 is attached to the processing section 105 of the swaging processing machine 100, the wire rod 11 is set on the processing section 105, and the outer periphery of the wire rod 11 is pressed by the mold 106 as illustrated in FIG. 4A. At that time, an attaching position of the mold 106 and arrangement of the wire rod 11 are adjusted such that a center line of the transfer surface 106a passes through a rotation central axis (central axis in the longitudinal direction) R of the wire rod 11. According to this, as illustrated in FIG. 4B, a portion on which the transfer surface 106a abuts of the outer periphery of the wire rod 11 is plastically deformed and the concave portion 13 is formed.

Figure 4C:
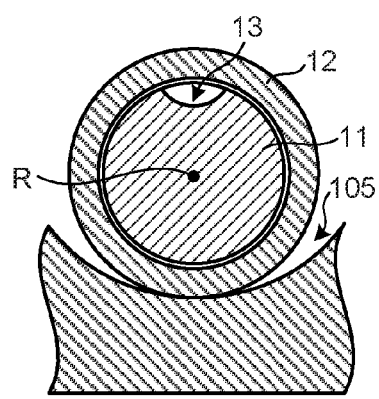

Subsequently, as illustrated in FIG. 4C, the wire rod 11 and the tubular member 12 are set on the processing section 105 in a state in which the tubular member 12 is overlaid on the wire rod 11 to cover the concave portion 13. At that time, it is preferable that the wire rod 11 is kept fixed to the swaging processing machine 100 such that a direction of the concave portion 13 is not changed from a state in FIG. 4B (upward) and the tubular member 12 is moved to be overlaid on the wire rod 11.

Figure 4D:
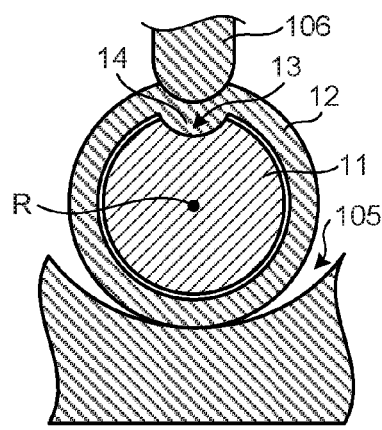

Subsequently, as illustrated in FIG. 4D, a portion of the tubular member 12 covering the concave portion 13 is pressed in a direction toward the concave portion 13 by the mold 106 for plastically deforming the tubular member 12 along the concave portion 13. According to this, the pipe joining body 10 illustrated in FIGS. 1A and 1B is obtained.

A pressing amount by the mold 106 at that time is not larger than the pressing amount by the mold 106 when the concave portion 13 is formed. According to this, the maximum displacement amount of the tubular member 12 by the plastic deformation when the deformed portion 14 is formed is not larger than the maximum displacement amount of the wire rod 11 by the plastic deformation when the concave portion 13 is formed and it is possible to prevent the deformed portion 14 from becoming thinner than the other portions. At that time, by using the same mold 106 as that when the concave portion 13 is formed, it is possible to deform the deformed portion 14 along the concave portion 13.

As described above, according to the first embodiment, the concave portion 13 is formed on the wire rod 11 by the plastic deformation and the deformed portion 14 is formed so as to enter the concave portion 13 by the plastic deformation of the tubular member 12 along the concave portion 13, so that the wire rod 11 and the tubular member 12 may be easily joined to each other. It is possible to keep the thickness in the deformed portion 14 the same as that in the other portions by making the maximum displacement amount of the tubular member 12 in the deformed portion 14 not larger than the maximum displacement amount of the wire rod 11 in the concave portion 13, so that deterioration in strength in the deformed portion 14 may be inhibited.

According to the first embodiment, the concave portion 13 is formed on the wire rod 11 in advance, so that even if the tubular member 12 has hardness lower than that of the wire rod 11, the members may be easily and certainly joined to each other. Herein, in general swaging processing, if the tubular member has hardness lower than that of the wire rod, there is a case in which even when the tubular member is swaged, the wire rod inserted therein is not plastically deformed and the joining is difficult; however, in the first embodiment, the wire rod 11 and the tubular member 12 may be certainly joined to each other.

According to the first embodiment, the concave portion 13 of the wire rod 11 is formed by the plastic deformation by using the swaging processing machine 100, so that the concave portion 13 may be formed with a high degree of accuracy even when the wire rod 11 is formed of a hard material or when the wire rod 11 is fine.

According to the first embodiment, the mold 106 including the same transfer surface 106a is used when the concave portion 13 of the wire rod 11 is formed and when the deformed portion 14 of the tubular member 12 is formed, so that it is possible to easily deform the deformed portion 14 along the concave portion 13 without changing the thickness thereof.

The above-described first embodiment may be carried out not only with the swaging processing machine 100 illustrated in FIG. 2 but also with a general swaging processing machine by using the mold 106 capable of partially pressing the outer periphery of the wire rod 11 and the tubular member 12.

In the above-described first embodiment, a step of forming the concave portion 13 on the wire rod 11 and a step of forming the deformed portion 14 on the tubular member 12 are performed by using one swaging processing machine 100. In this case, a positioning step of aligning a position of the concave portion 13 (direction of the wire rod 11) to the mold 106 is not necessary when forming the deformed portion 14. However, the steps may also be performed by using different swaging processing machines.

First Modification

Next, a first modification of the first embodiment of the present invention will be described.

Figure 5:
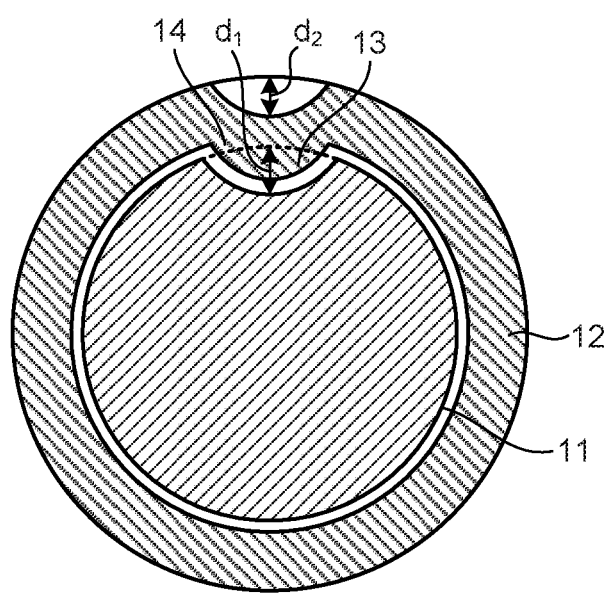
FIG. 5 is a cross-sectional view illustrating a structure of a pipe joining body according to a modification of the first embodiment of the present invention.

FIG. 5 is a cross-sectional view illustrating a structure of a pipe joining body according to the first modification. Although the maximum displacement amount $d_1$ of the wire rod 11 in the concave portion 13 is made substantially the same as the maximum displacement amount $d_2$ of the tubular member 12 in the deformed portion 14 in the above-described first embodiment, $d_1 > d_2$ may also be satisfied as long as the deformed portion 14 is not dropped out from the concave portion 13.

Second Embodiment

Next, a second embodiment of the present invention will be described.

Figure 6A:
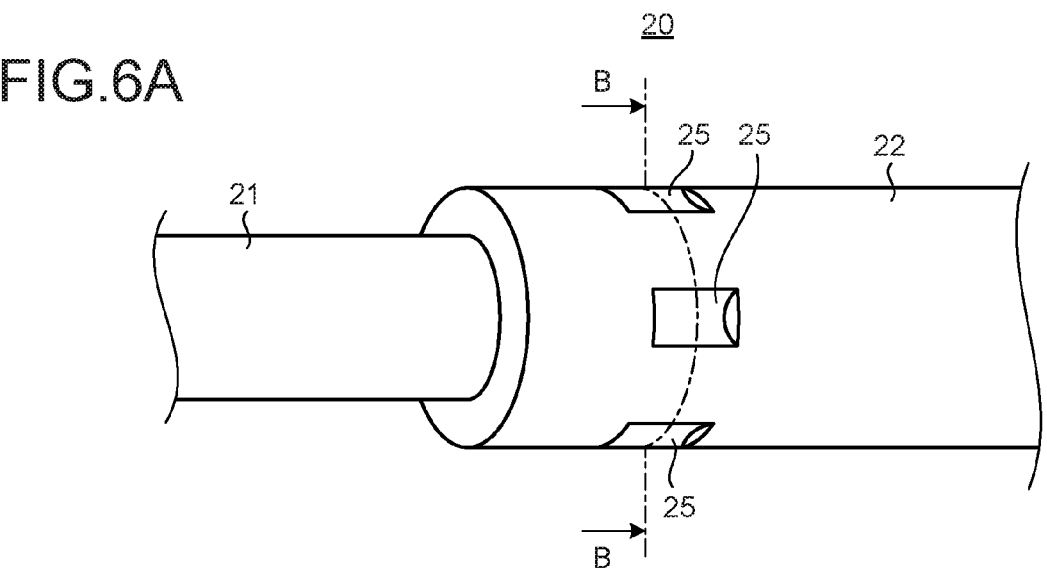
FIGS. 6A and 6B are schematic views illustrating a structure of a pipe joining body according to a second embodiment of the present invention.
Figure 6B:
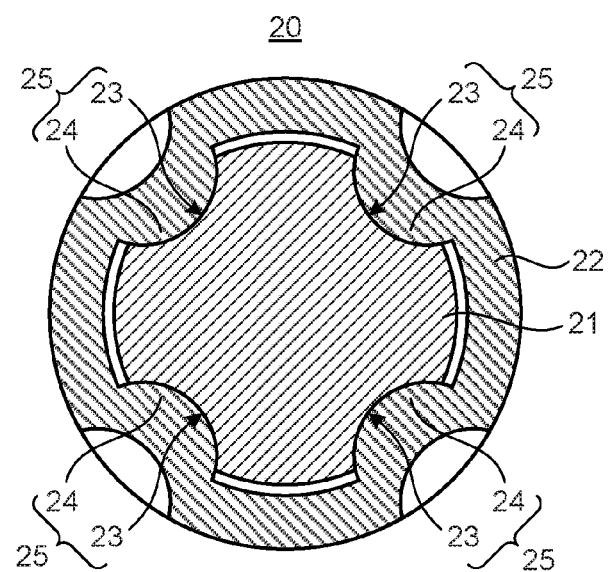

FIGS. 6A and 6B are schematic views illustrating a structure of a pipe joining body according to the second embodiment. FIG. 6A is a perspective, external view of the pipe joining body and FIG. 6B is a cross-sectional view taken along B-B in FIG. 6A. As illustrated in FIGS. 6A and 6B, a pipe joining body 20 according to the second embodiment is provided with a wire rod 21 and a tubular member 22 formed of metal or alloy. Materials of the wire rod 21 and the tubular member 22 are similar to those of the wire rod 11 and the tubular member 12 in the first embodiment.

Four concave portions 23 formed by plastic deformation are provided at four locations on an outer periphery of the wire rod 21. Four deformed portions 24 formed by the plastic deformation are provided at four locations on an outer periphery of the tubular member 22 so as to enter the four concave portions 23, respectively. Shapes, dimensions, and maximum displacement amounts by the plastic deformation of the concave portions 23 and the deformed portions 24 are similar to those of the first embodiment. In this manner, by providing the concave portions 23 and the deformed portions 24 forming joining portions 25 to join the wire rod 21 and the tubular member 22 to each other at four locations, it is possible to more tightly join the members.

Figure 7A:
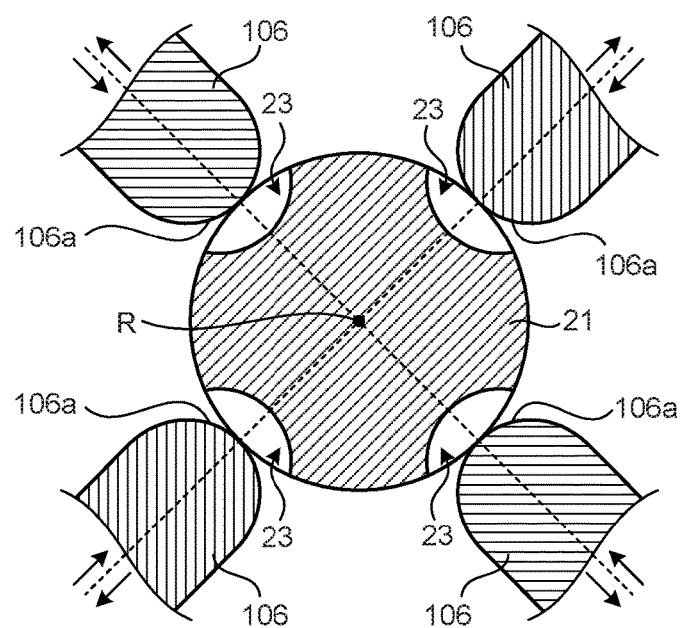
FIGS. 7A and 7B are schematic diagrams for illustrating a joining method according to the second embodiment of the present invention.
Figure 7B:
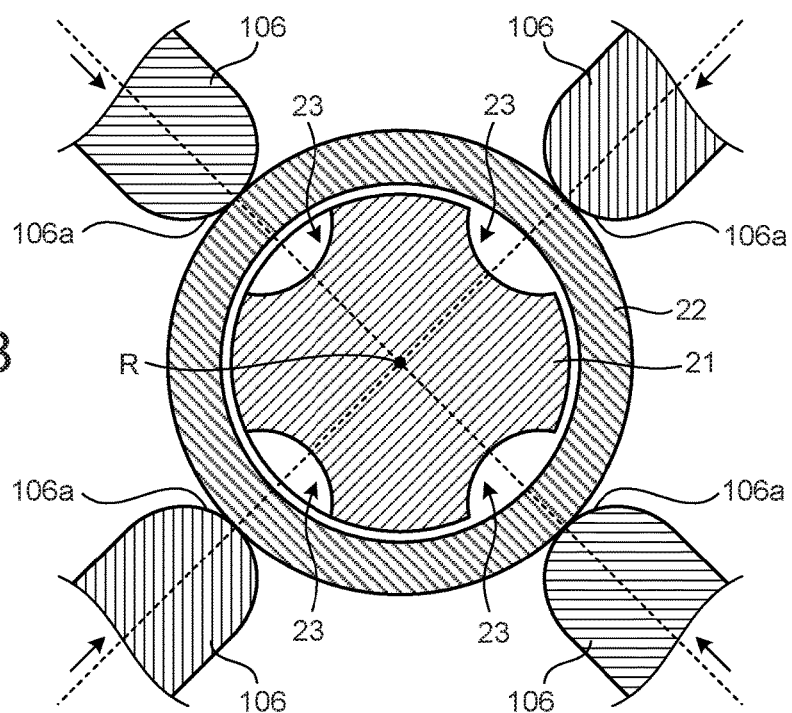

FIGS. 7A and 7B are schematic diagrams for illustrating a joining method according to the second embodiment. When the joining portions 25 are provided at four locations, four molds 106 (refer to FIG. 3) are attached to a processing section 105 of a swaging processing machine 100 illustrated in FIG. 2 in a rotationally symmetrical manner at intervals of 90 degrees such that each transfer surface 106a faces a rotation central axis R. Then, the wire rod 21 is set on the processing section 105 and the outer periphery of the wire rod 21 is pressed in a direction toward the rotation central axis R by the four molds 106 as illustrated in FIG. 7A. According to this, a portion on which the transfer surface 106a abuts is plastically deformed and the concave portion 23 is formed. FIG. 7A illustrates a state in which the mold 106 is separated from the concave portion 23 after the concave portion 23 is formed.

Subsequently, in a state in which the tubular member 22 is overlaid on the wire rod 21 to cover the concave portion 23, the wire rod 21 and the tubular member 22 are set on the processing section 105. Then, as illustrated in FIG. 7B, portions of the tubular member 22 covering the four concave portions 23 are pressed by the four molds 106, respectively, such that the tubular member 22 is plastically deformed along the concave portion 23. According to this, the pipe joining body 20 illustrated in FIGS. 6A and 6B is obtained.

Second Modification

Next, a second modification of the second embodiment of the present invention will be described.

Figure 8:
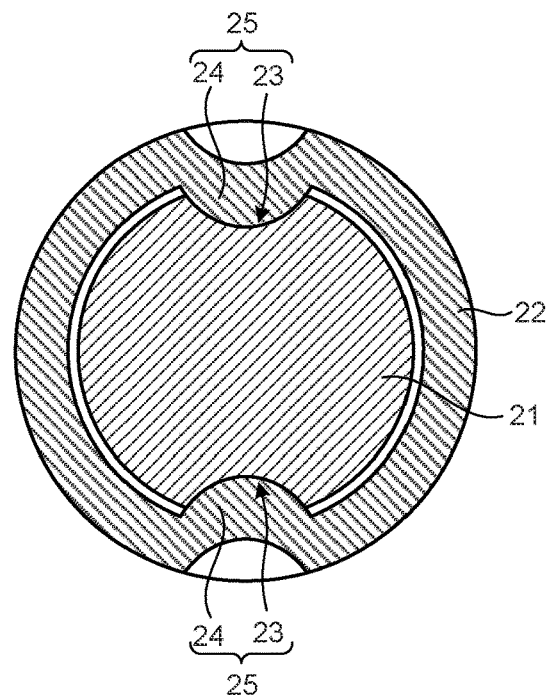
FIG. 8 is a cross-sectional view illustrating a structure of a pipe joining body according to a modification of the second embodiment of the present invention.

FIG. 8 is a cross-sectional view illustrating a structure of a pipe joining body according to the second modification. Although the joining portions 25 formed of the concave portions 23 and the deformed portions 24 are provided at four locations in the above-described second embodiment, the joining portions 25 may also be provided at two locations as illustrated in FIG. 8. In this case, two molds 106 are attached to a processing section 105 of a swaging processing machine 100 illustrated in FIG. 2 such that transfer surfaces 106a are opposed to each other and processing similar to that of the second embodiment is performed.

When the joining portions 25 are provided at three locations or five or more locations, the desired number of molds 106 may be evenly arranged on the processing section 105 in a rotationally symmetrical manner according to the number such that the transfer surfaces 106a face a rotation central axis R and the processing similar to that of the second embodiment may be performed.

Third Embodiment

Next, a third embodiment of the present invention will be described.

Figure 9:
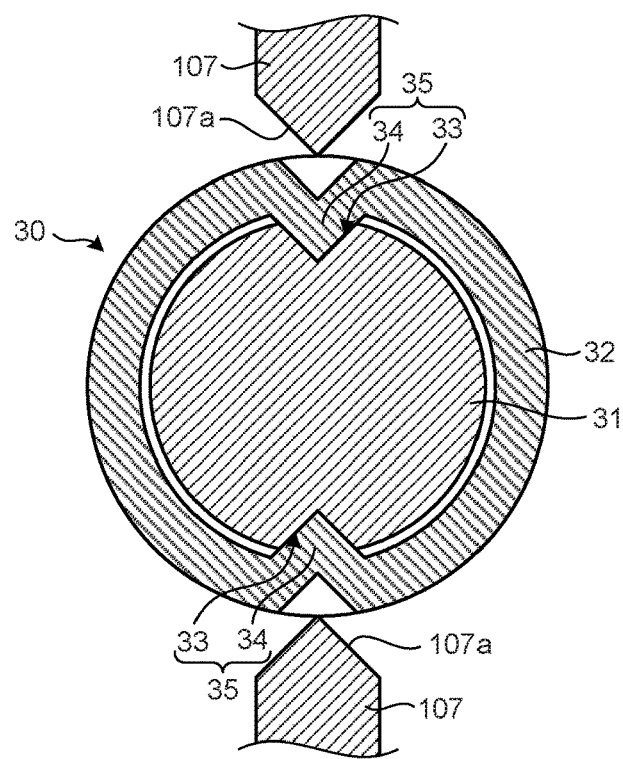
FIG. 9 is a cross-sectional view illustrating a structure of a pipe joining body according to a third embodiment of the present invention.

FIG. 9 is a cross-sectional view illustrating a structure of a pipe joining body according to the third embodiment. As illustrated in FIG. 9, a pipe joining body 30 according to the third embodiment is provided with a wire rod 31 and a tubular member 32 formed of metal or alloy. Materials of the wire rod 31 and the tubular member 32 are similar to those of the wire rod 11 and the tubular member 12 in the first embodiment.

A concave portion 33 formed by plastic deformation is provided on an outer periphery of the wire rod 31. The concave portion 33 has a substantially rectangular shape when the wire rod 31 before the joining is viewed from a side surface and has a wedge shape in cross section orthogonal to a longitudinal direction of the wire rod 31. A deformed portion 34 formed by the plastic deformation is provided on an outer periphery of the tubular member 32 along the concave portion 33. Similar to the concave portion 33, the deformed portion 34 also has a substantially rectangular shape when the tubular member 32 is viewed from a side surface and has a wedge shape in cross section orthogonal to a longitudinal direction of the tubular member 32.

As illustrated in FIG. 9, it is possible to fabricate such pipe joining body 30 by attaching a mold 107 including a processing surface 107a in a wedge shape to a processing section 105 of a swaging processing machine 100 illustrated in FIG. 2 and perform processing as in the second embodiment. The number of locations where joining portions 35 formed of the concave portions 33 and the deformed portions 34 are arranged is not limited to two; the portions may also be provided at only one location as in the first embodiment or the portions may be provided at three or more locations.

In this manner, a cross-sectional shape of the concave portion formed on the wire rod and the deformed portion formed on the tubular member (that is to say, a shape of a transfer surface of the mold) is not limited to an arc-like shape described in the first and second embodiments; the wedge shape and various other shapes may also be applied as long as the concave portion and the deformed portion may be formed on the wire rod and a cylindrical member, respectively.

A side surface shape of the concave portion and the deformed portion (that is to say, an upper surface shape of the mold) is not limited to the rectangular shape; various shapes such as a square, a trapezoid, and a polygon may also be applied.

Fourth Embodiment

Next, a fourth embodiment of the present invention will be described.

Figure 10A:
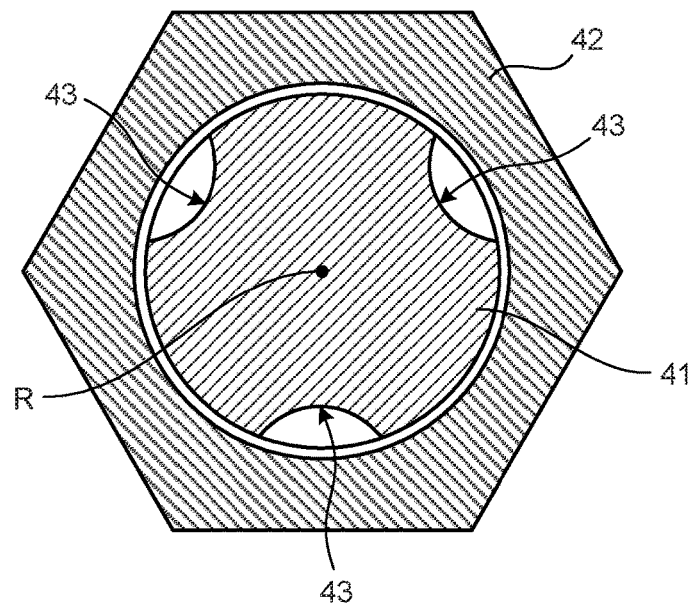
FIGS. 10A and 10B are cross-sectional views for illustrating a pipe joining body according to a fourth embodiment of the present invention.
Figure 10B:
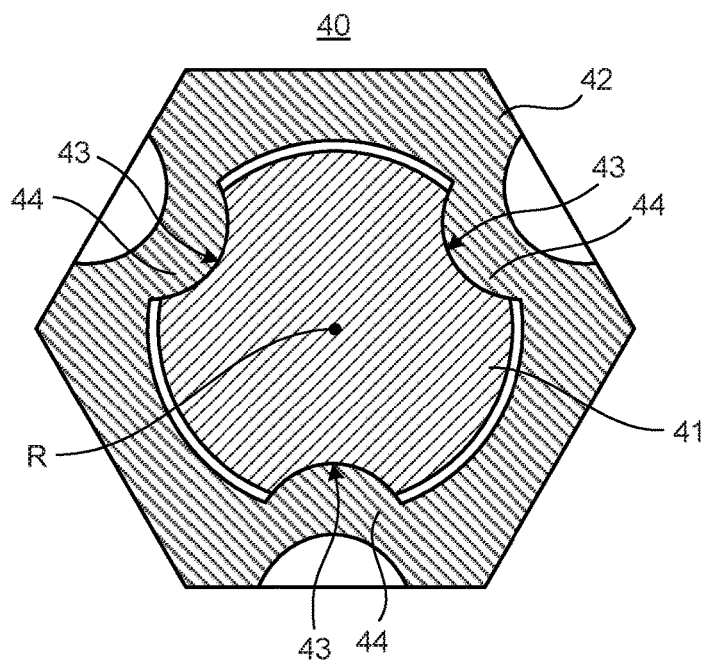

FIGS. 10A and 10B are cross-sectional views for illustrating a pipe joining body according to the fourth embodiment. In the above-described first to third embodiments, the cylindrical tubular members 12, 22, and 32 are joined to the columnar wire rods 11, 21, and 31, respectively. However, the shape of the tubular member is not limited to the cylindrical shape. For example, as illustrated in FIG. 10A, a tubular member 42 having a columnar inner peripheral surface and a polygonal columnar (for example, hexagonal columnar) outer peripheral surface may be joined to a columnar wire rod 41.

In this case, a concave portion 43 is formed on the wire rod 41 by using a mold 106 illustrated in FIG. 3 and the tubular member 42 is overlaid on the wire rod 41 to form a deformed portion 44 by using the same mold 106 in a swaging processing machine 100 illustrated in FIG. 2. At that time, a pressing direction by the mold 106 is always a direction toward a rotation central axis R. According to this, a pipe joining body 40 illustrated in FIG. 10B is fabricated.

Although the inner peripheral surface of the tubular member 42 is in the columnar shape in the fourth embodiment, when the outer peripheral surface of the wire rod 41 is in the polygonal columnar shape, the inner peripheral surface of the tubular member 42 may also have the same polygonal columnar shape.

Fifth Embodiment

Next, a fifth embodiment of the present invention will be described.

Figure 11A:
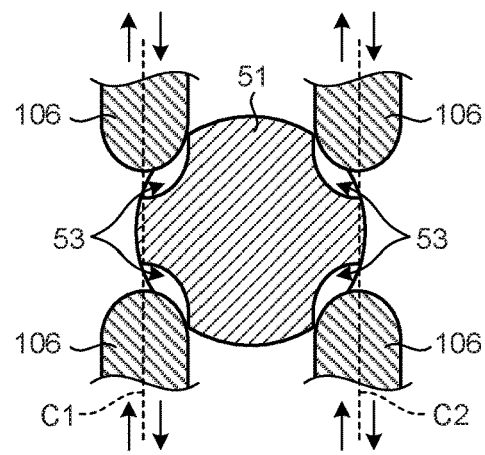
FIGS. 11A to 11C are schematic diagrams for illustrating a joining method according to a fifth embodiment of the present invention.
Figure 11B:
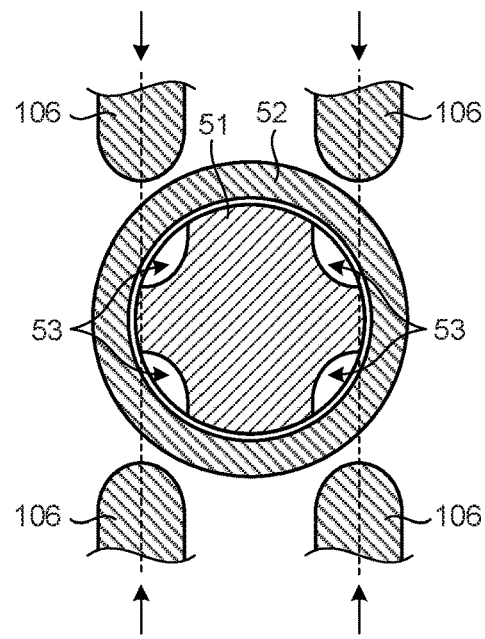
Figure 11C:
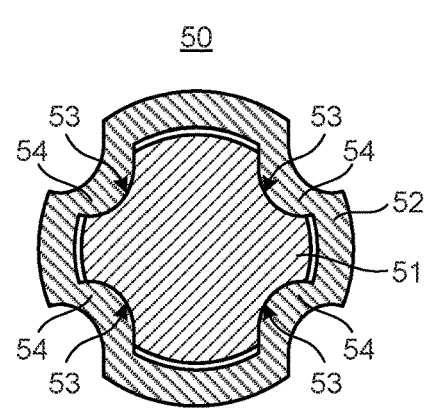

FIGS. 11A to 11C are schematic diagrams for illustrating a joining method according to the fifth embodiment. In the above-described first to fourth embodiments, the wire rods 11, 21, 31, and 41 and the tubular members 12, 22, 32, and 42 are pressed in the direction toward the rotation central axis R when forming the concave portions 13, 23, 33, and 43 and the deformed portions 14, 24, 34, and 44, respectively, by the mold 106 (refer to FIG. 3) and the mold 107 (refer to FIG. 9). However, if the concave portion may be formed on the wire rod and the deformed portion may be formed on the tubular member so as to enter the concave portion, the pressing direction is not limited to the direction toward the rotation central axis R.

For example, as illustrated in FIGS. 11A to 11C, the pressing directions of the four molds 106 may be parallel to one another. In detail, as illustrated in FIG. 11A, two pairs of two molds 106 are arranged so as to be opposed to each other with coincident center lines C1 and C2 and a wire rod 51 is pressed by the molds 106 along the center lines C1 and C2 to form concave portions 53. FIG. 11A illustrates a state in which the mold 106 is separated from the concave portion 53 after the concave portion 53 is formed.

Subsequently, as illustrated in FIG. 11B, the wire rod 51 is inserted into a tubular member 52 and the tubular member 52 is pressed by the molds 106 arranged as in FIG. 11A along center lines C1' and C2' to form the deformed portions 54. According to this, a pipe joining body 50 illustrated in FIG. 11C is obtained.

Sixth Embodiment

Next, a sixth embodiment of the present invention will be described.

Although the concave portion (for example, the concave portion 13 illustrated in FIGS. 1A and 1B) of the wire rod and the deformed portion (for example, the deformed portion 14 illustrated in FIGS. 1A and 1B) of the tubular member are formed by using the mold of the same shape (for example, the mold 106 illustrated in FIG. 3) in the above-described first to fifth embodiments, it is also possible to form the concave portion and the deformed portion by using the molds having different shapes and curvatures.

For example, it is also possible to form the concave portion of the wire rod by using the mold 106 illustrated in FIG. 3 and form the deformed portion of the tubular member by using a mold 107 illustrated in FIG. 9, for example. In this case, the concave portion has an arc-like shape and the deformed portion has a wedge shape in cross section orthogonal to a longitudinal direction of the wire rod and the tubular member.

Alternatively, also when the mold including a transfer surface with an arc-like shaped cross section as the mold 106 is used, it is also possible to form the deformed portion of the tubular member by using a mold with a larger curvature (smaller curvature radius) than that of the mold used when the concave portion of the wire rod is formed.

In any case, the shapes of the concave portion and the deformed portion, that is to say, the shapes of the molds used when the concave portion and the deformed portion are formed and a combination thereof are not limited as long as a maximum displacement amount of the tubular member by plastic deformation when the deformed portion is formed is the same as or smaller than a maximum displacement amount of the wire rod by plastic deformation when the concave portion is formed.

Seventh Embodiment

Next, a seventh embodiment of the present invention will be described.

Figure 12:
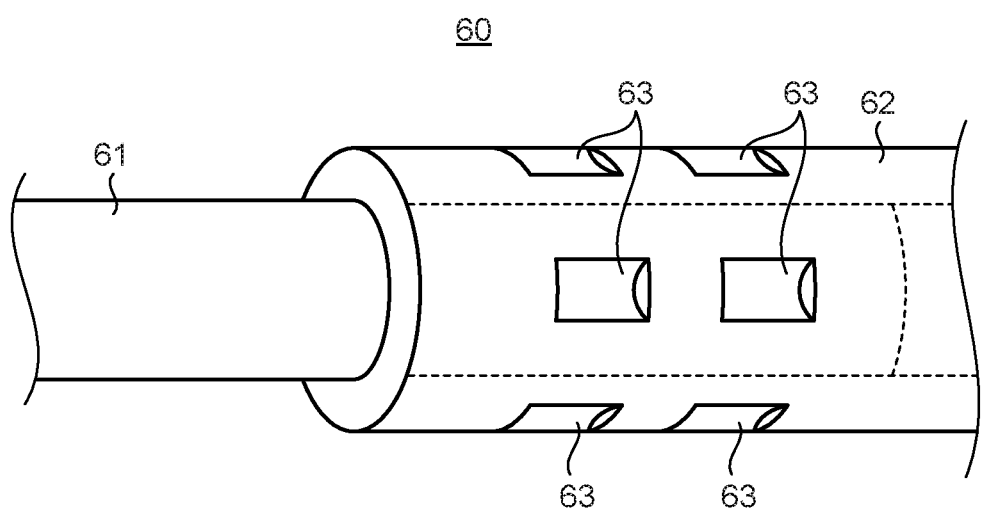
FIG. 12 is a perspective, external view of a pipe joining body according to a seventh embodiment of the present invention.

FIG. 12 is a perspective view illustrating an exterior appearance of a pipe joining body according to the seventh embodiment. Although the joining portions 15 and 25 which join the wire rods 11 and 21 to the tubular members 12 and 22 are provided in only one column in the longitudinal direction of the tubular members 12 and 22 in the above-described first or second embodiment, it is also possible to provide a plurality of columns of the joining portions in the longitudinal direction.

For example, in a pipe joining body 60 illustrated in FIG. 12, joining portions 63 which join a wire rod 61 to a tubular member 62 are provided in two columns in the longitudinal direction. Each joining portion 63 is formed of a concave portion formed by plastic deformation of a part of the wire rod 61 and a deformed portion formed by the plastic deformation of the tubular member 62 such that a part of the tubular member 62 enters the concave portion (not illustrated) as in the first and second embodiments.

In this manner, by providing a plurality of columns of the joining portions 63 in the longitudinal direction, joining force between the wire rod 61 and the tubular member 62 may be made stronger.

Eighth Embodiment

Next, an eighth embodiment of the present invention will be described.

Figure 13:
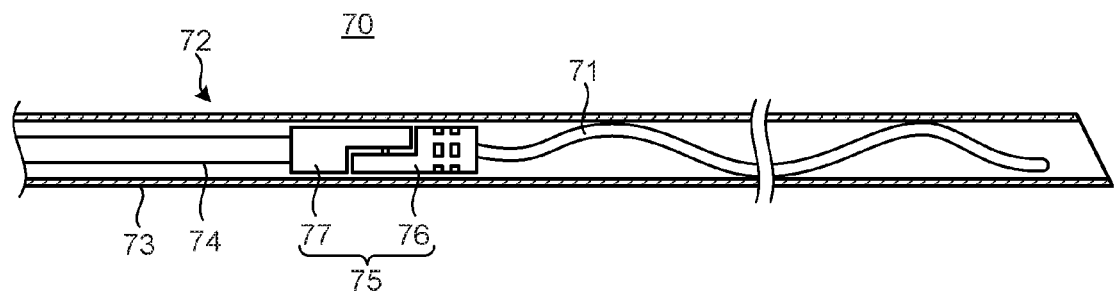
FIG. 13 is a schematic diagram illustrating an internal structure of a treatment tool according to an eighth embodiment of the present invention.

FIG. 13 is a schematic diagram illustrating an internal structure of a treatment tool according to the eighth embodiment. The treatment tool according to the eighth embodiment is a tool inserted into a living body through a treatment tool channel of an endoscope for performing treatment in the living body.

As illustrated in FIG. 13, a treatment tool 70 according to the eighth embodiment is provided with a tissue clamping tool 71 which fixes tissue in the living body and an applicator 72 for retaining the tissue clamping tool 71 in a desired position in the living body. Out of them, the applicator 72 is provided with an insertion needle tube 73 inserted into the tissue in the living body, a pusher 74 which pushes out the tissue clamping tool 71 from the applicator 72, and a connecting portion 75 which connects the pusher 74 to the tissue clamping tool 71. In FIG. 13, only the insertion needle tube 73 is illustrated in cross section and other elements are illustrated as viewed from a side surface.

The tissue clamping tool 71 being a highly elastic metallic wire rod wound into a coil shape is inserted into the insertion needle tube 73 in an extended state before this is retained in the living body. The tissue clamping tool 71 is formed of an alloy material having a shape-memory characteristic and a superelastic characteristic such as nickel-titanium alloy (NiTi).

The shape-memory characteristic is a characteristic that a shape deformed into an arbitrary shape is recovered to the shape before deformation when being heated to an Af point (transformation finishing temperature at which a martensite phase at the time of heating is transformed to an austenite phase). Alloy the Af point of which is not higher than normal temperature recovers to its original shape without especially being heated, so that this is also referred to as superelastic alloy. Nickel-titanium alloy may be assigned with the shape-memory characteristic and the superelastic characteristic by control of the Af point by a composition ratio between nickel and titanium, a condition of thermal treatment and the like.

Herein, a metal material such as stainless steel (SUS) or an alloy material is conventionally widely used for the treatment tool used in the living body such as the tissue clamping tool. In contrast, the treatment channel of the endoscope has a significantly small diameter of approximately two to four millimeters, so that it is required to make the treatment tool inserted therethrough into the living body to have a smaller diameter. When the tissue clamping tool is formed of SUS under such a condition, it is significantly difficult to recover the tissue clamping tool extended to be accommodated in the needle tube of the small diameter to its designed shape in the living body, so that it is difficult to allow the same to sufficiently exert its function as the tissue clamping tool.

In contrast, nickel-titanium alloy with memorized coil shape extended to be accommodated in the insertion needle tube 73 of the small diameter may be recovered to its designed shape in the living body due to the shape-memory characteristic and the superelastic characteristic, so that this may sufficiently exert the function as the tissue clamping tool 71.

Please refer to JP 2009-66408 A and JP 2010-17542 A, for example, for an action when the tissue clamping tool 71 is retained in the living body.

The insertion needle tube 73 is the needle tube insertable into the tissue in the living body having a distal end portion (not illustrated) sharply formed. The insertion needle tube 73 accommodates the tissue clamping tool 71 in the extended state and carries the tissue clamping tool 71 to an affected site in the living body by operation on the treatment tool 70.

The pusher 74 formed into a shaft shape is inserted inside the insertion needle tube 73 so as to be movable. The pusher 74 pushes out the tissue clamping tool 71 accommodated in the insertion needle tube 73 from a distal end of the insertion needle tube 73 through the connecting portion 75 by the operation on the treatment tool 70.

Figure 14:
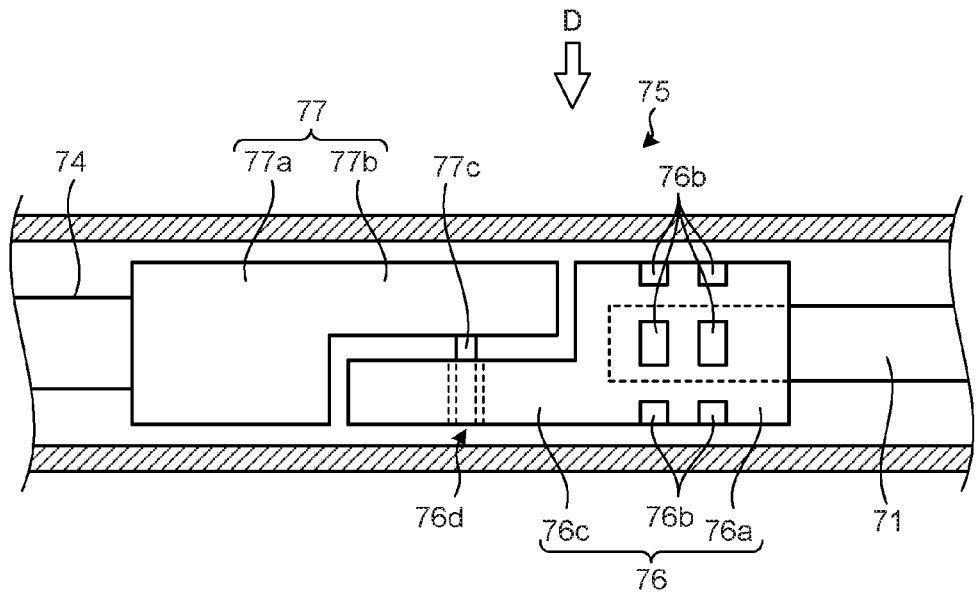
FIG. 14 is a schematic diagram illustrating a connecting portion illustrated in FIG. 13 in an enlarged manner.

FIG. 14 is a schematic diagram illustrating the connecting portion 75 illustrated in FIG. 13 in an enlarged manner. In FIG. 14 also, only the insertion needle tube 73 is illustrated in cross section and other elements are illustrated as viewed from a side surface. As illustrated in FIG. 14, the connecting portion 75 includes a clamping tool side connecting portion 76 joined to the tissue clamping tool 71 and a pusher side connecting portion 77 joined to the pusher 74. The clamping tool side connecting portion 76 and the pusher side connecting portion 77 are formed of metal or alloy excellent in biocompatibility such as stainless steel (SUS).

Figure 15:
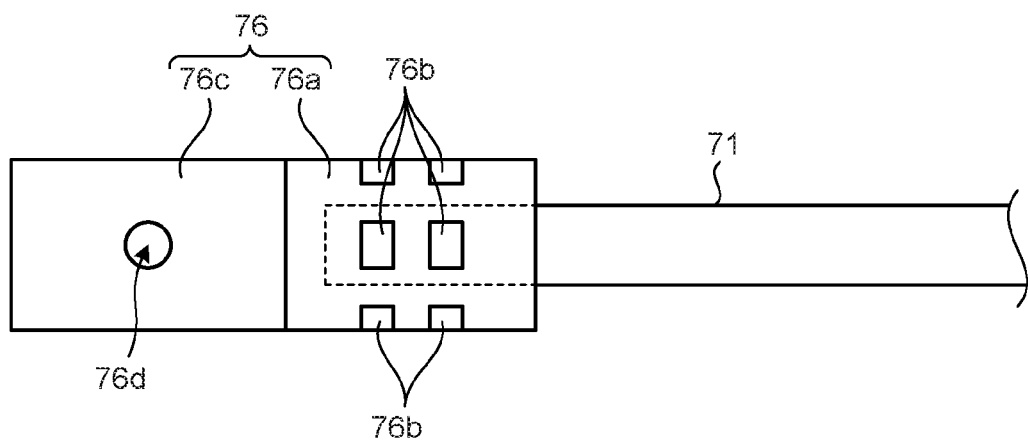
FIG. 15 is a schematic view of a clamping tool side connecting portion illustrated in FIG. 14, viewed in an arrow D direction.

FIG. 15 is a schematic view of the clamping tool side connecting portion 76 illustrated in FIG. 14, viewed in an arrow D direction. As illustrated in FIGS. 14 and 15, the clamping tool side connecting portion 76 has a shape obtained by cutting out a part of a column as a whole. A columnar portion 76a of the clamping tool side connecting portion 76 has a bottomed tubular shape and an end of the tissue clamping tool 71 is inserted into the columnar portion 76a. The tissue clamping tool 71 and the columnar portion 76a are joined to each other by a plurality of joining portions 76b. A structure of each joining portion 76b is similar to that of a joining portion 15 illustrated in FIGS. 1A and 1B. Although four joining portions 76b are provided in each of two columns in a longitudinal direction in the eighth embodiment, the number of the joining portions 76b is not limited thereto. A hole 76d is formed on a semicircular columnar portion 76c of the clamping tool side connecting portion 76.

In contrast, the pusher side connecting portion 77 has a shape obtained by cutting out a part of a column having a diameter comparable to that of the above-described clamping tool side connecting portion 76. The pusher side connecting portion 77 is joined to a distal end of the pusher 74 in the columnar portion 77a. The pusher side connecting portion 77 and the pusher 74 may be joined to each other by a method similar to that of the joining portion 15 of the first embodiment or by another well-known method. A grappling pin 77c insertable into the hole 76d of the clamping tool side connecting portion 76 is provided on the semicircular columnar portion 77b of the pusher side connecting portion 77.

The clamping tool side connecting portion 76 and the pusher side connecting portion 77 are accommodated in the insertion needle tube 73 in a state in which a planer portions of the semicircular columnar portions 76c and 77b are opposed to each other and the grappling pin 77c is inserted into the hole 76d.

Figure 16:
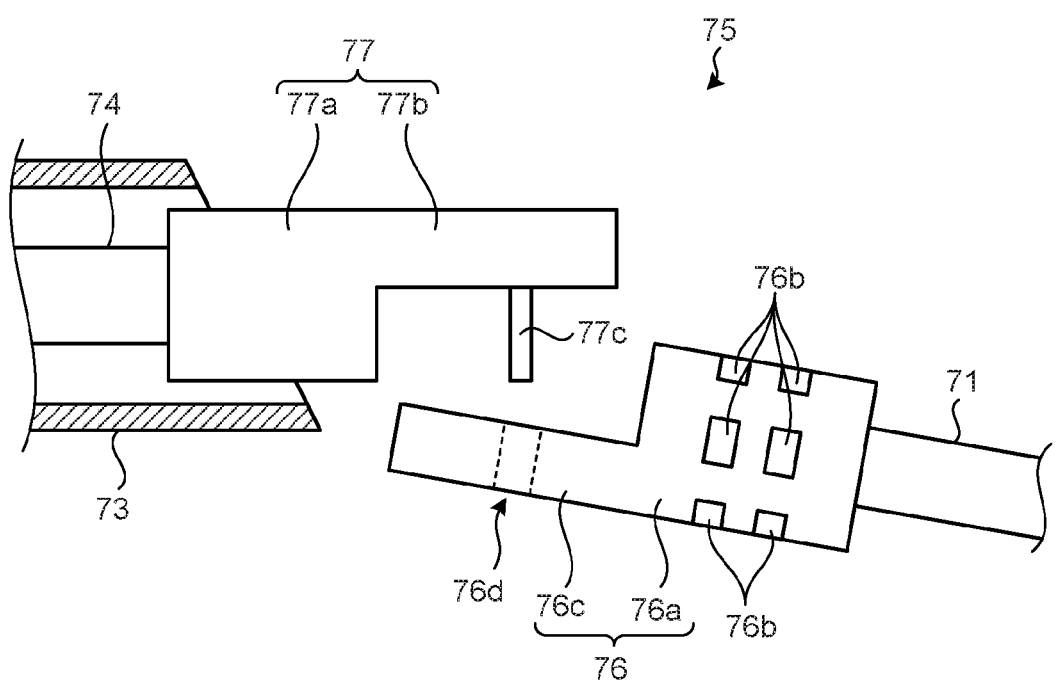
FIG. 16 is a schematic diagram for illustrating a method of using the treatment tool illustrated in FIG. 13.

Next, a method of using the treatment tool 70 will be described with reference to FIGS. 13 and 16. FIG. 16 is a schematic diagram for illustrating the method of using the treatment tool 70. When the treatment tool 70 is used, the treatment tool 70 is inserted into the living body through the treatment tool channel of the endoscope and the distal end of the insertion needle tube 73 is inserted into the affected site. In this state, the tissue clamping tool 71 is pushed out from the distal end of the insertion needle tube 73 by the pusher 74. At that time, the pusher 74 is connected to the tissue clamping tool 71 through the connecting portion 75, so that the tissue clamping tool 71 may be certainly pushed out and a pushing amount may be easily controlled. The tissue clamping tool 71 pushed into the living body from the insertion needle tube 73 is recovered to its original coil shape by the shape-memory characteristic or the superelastic characteristic to clamp the tissue of the affected site.

As illustrated in FIG. 16, when the clamping tool side connecting portion 76 joined to the end of the tissue clamping tool 71 is pushed out of the insertion needle tube 73, the grappling pin 77c is removed from the hole 76d and the connection between the clamping tool side connecting portion 76 and the pusher side connecting portion 77 is released. According to this, the tissue clamping tool 71 and the clamping tool side connecting portion 76 joined thereto are retained in the living body. On the other hand, the pusher side connecting portion 77 is retracted in the insertion needle tube 73 to be removed from the living body together with the insertion needle tube 73.

Herein, reference will be made to a reason why the tissue clamping tool 71 and the clamping tool side connecting portion 76 are joined to each other by the joining portion 76b by the joining method similar to that of the first embodiment. First, since the tissue clamping tool 71 and the clamping tool side connecting portion 76 are retained in the living body, solder (for example, Sn—Ag—Cu solder) and adhesive having a problem with biocompatibility and corrosion resistance cannot be used.

In general, welding forms an intermetallic compound in a weld structure. For example, welding nickel-titanium alloy and stainless steel forms FeTi alloy as the intermetallic compound. Such intermetallic compound is brittle, so that the weld structure has low impact load tolerance. Therefore, the tissue clamping tool 71 cannot be joined to the clamping tool side connecting portion 76 by welding.

Under such circumstance, for joining the tissue clamping tool 71 to the clamping tool side connecting portion 76, swaging processing in which a member other than them is not used is suitable. However, as described above, nickel-titanium alloy having a characteristic suitable for the tissue clamping tool 71 is significantly hard, so that it is difficult to perform general swaging processing.

It is also considered that a locking groove for swaging the clamping tool side connecting portion 76 is formed in advance on the tissue clamping tool 71 by cutting and the like; however, since nickel-titanium alloy is significantly hard as described above, cutting by a cutting knife of general high-speed steel is difficult. In addition, it is significantly difficult to perform fine and highly accurate cutting work on the wire rod of a small diameter such as the tissue clamping tool 71. Especially, when the tissue clamping tool 71 and the clamping tool side connecting portion 76 are joined to each other, high joining strength is required, so that the cutting which cannot obtain positional accuracy of the locking groove cannot be used.

On the other hand, in the eighth embodiment, as described in the above-described first embodiment, a concave portion is formed by plastic deformation of a part of the wire rod by using a swaging processing machine and a mold and a part of the tubular member is plastically deformed so as to enter the concave portion by using the similar mold, so that the wire rod (tissue clamping tool 71) and the tubular member (clamping tool side connecting portion 76) may be easily and certainly joined to each other. At that time, a maximum displacement amount of the tubular member by the plastic deformation is made not larger than a maximum displacement amount of the wire rod by the plastic deformation, so that it becomes possible to tightly join the members without partial deterioration in strength in the joining portion (joining portion 76b).

Although the joining portions 76b are provided in two columns at four locations on a circumference in the eighth embodiment, the number and arrangement of the joining portions 76b are not limited thereto. For example, the portions may be provided in one column at one or more locations on the circumference or provided in three or more columns. The joining portion 76b may be formed by using a mold 107 having a wedge shape as in the third embodiment, or a pressing direction when forming the concave portion and the deformed portion may be other than a direction toward a rotation central axis as in the fifth embodiment.

According to some embodiments, a concave portion is formed by plastically deform a part of an outer periphery of a wire rod, a deformed portion is formed by plastically deform a part of a tubular member along the concave portion, and a maximum displacement amount of the tubular member by the plastic deformation is not larger than a maximum displacement amount of the wire rod by the plastic deformation when the concave portion is formed. With this structure, it is possible to tightly and easily join the wire rod to the tubular member without partial deterioration of strength in the tubular member.

The above-described present invention is not limited to the first to eighth embodiments and the modifications thereof and various inventions may be made by appropriately combining a plurality of elements disclosed in the embodiments and modifications. For example, it is possible to remove some elements from all the elements described in the embodiments and the modifications or appropriately combine the elements described in the different embodiments and modifications.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A method of manufacturing a structure including a wire rod and a tubular member, the method comprising:
forming at least one concave portion by plastically deforming a part of an outer periphery of the wire rod; and
forming, in the tubular member, at least one deformed portion that enters the at least one concave portion by inserting the wire rod into the tubular member and by pressing a portion of the tubular member covering the at least one concave portion from an outer periphery of the tubular member toward the at least one concave portion to plastically deform the portion of the tubular member,
wherein:
a maximum displacement amount of the tubular member in forming the deformed portion is smaller than a maximum displacement amount of the wire rod in forming the concave portion, the forming of the concave portion includes bringing a transfer mold having a convex transfer surface into contact with the part of the outer periphery of the wire rod and pressing the wire rod with the convex transfer surface of the transfer mold, and the forming of the deformed portion includes bringing a transfer mold having a transfer surface of a same shape as the convex transfer surface of the transfer mold used for the wire rod, into contact with the outer periphery of the tubular member and pressing the outer periphery of the tubular member with the transfer surface of the transfer mold.

2. The method according to claim 1, wherein:

the forming of the concave portion includes pressing the transfer mold having the convex transfer surface toward a central axis in a longitudinal direction of the wire rod, and the forming of the deformed portion includes pressing the transfer mold having the transfer surface of the same shape as the convex transfer surface of the transfer mold used for the wire rod, toward the central axis in the longitudinal direction of the wire rod.

3. A method of manufacturing a structure including a wire rod and a tubular member, the method comprising:

forming at least one concave portion by plastically deforming a part of an outer periphery of the wire rod; and forming, in the tubular member, at least one deformed portion that enters the at least one concave portion by inserting the wire rod into the tubular member and by pressing a portion of the tubular member covering the at least one concave portion from an outer periphery of the tubular member toward the at least one concave portion to plastically deform the portion of the tubular member, wherein:

a maximum displacement amount of the tubular member in forming the deformed portion is smaller than a maximum displacement amount of the wire rod in forming the concave portion, and a hardness of the tubular member is lower than hardness of the wire rod.

4. The method according to claim 1, wherein:

forming the at least one concave portion comprises forming at least two of the concave portions in the wire rod;

forming the at least one deformed portion comprises forming at least two of the deformed portions in the tubular member; and the deformed portions in the tubular member respectively enter the concave portions in the wire rod.

5. The method according to claim 1, wherein:

forming the at least one concave portion comprises forming four of the concave portions in the wire rod, at rotationally symmetric positions around the wire rod;

forming the at least one deformed portion comprises forming four of the deformed portions in the tubular member, at rotationally symmetric positions around the tubular member; and the deformed portions in the tubular member respectively enter the concave portions in the wire rod.

6. The method according to claim 1, wherein:

the concave portion of the wire rod is formed to have an arc shape, in a cross-section orthogonal to a longitudinal direction of the wire rod; and the deformed portion of the tubular member is formed to have an arc shape, in a cross-section orthogonal to a longitudinal direction of the wire rod.

7. The method according to claim 1, wherein:

the concave portion of the wire rod is formed to have a wedge shape, in a cross-section orthogonal to a longitudinal direction of the wire rod; and the deformed portion of the tubular member is formed to have a wedge shape, in a cross-section orthogonal to a longitudinal direction of the wire rod.

8. The method according to claim 1, wherein:

before concave portion is formed, the wire rod has a cylindrical shape; and before the deformed portion is formed, the tubular member has a hollow cylindrical shape.

9. The method according to claim 1, wherein:

before concave portion is formed, the wire rod has a cylindrical shape;

before the deformed portion is formed, the tubular member has a cylindrical inner periphery; and before the deformed portion is formed, the tubular member has a polygonal outer periphery.

* * * * *